United States Patent
Shiwaku

(10) Patent No.: US 11,246,512 B2
(45) Date of Patent: Feb. 15, 2022

(54) MEASURING APPARATUS, COMPUTER READABLE MEDIUM STORING MEASURING PROGRAM AND MEASURING METHOD

(71) Applicant: ARKRAY, Inc., Kyoto (JP)

(72) Inventor: Rikiya Shiwaku, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 677 days.

(21) Appl. No.: 16/025,506

(22) Filed: Jul. 2, 2018

(65) Prior Publication Data
US 2019/0008426 A1  Jan. 10, 2019

(30) Foreign Application Priority Data

Jul. 4, 2017 (JP) .............................. JP2017-131324
Jun. 28, 2018 (JP) .............................. JP2018-123529

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/1451* (2013.01); *A61B 5/1495* (2013.01);
(Continued)

(58) Field of Classification Search
CPC ... A61B 5/1451; A61B 5/1495; A61B 5/4839; A61B 2560/0223; A61B 5/157;
(Continued)

(56) References Cited

U.S. PATENT DOCUMENTS 4,206,755 A 6/1980 Klein
2005/0004439 A1\* 1/2005 Shin ................... A61B 5/14532
600/365

(Continued)

FOREIGN PATENT DOCUMENTS

CN  10277073 A  11/2012

OTHER PUBLICATIONS

Extended European Search Report issued in corresponding European Patent Application No. 18181541.6 dated Dec. 3, 2018.
Office Action and Search Report issued in counterpart Chinese Patent Application No. 201810720698.2 dated Dec. 20, 2021.

*Primary Examiner* — Shogo Sasaki
(74) *Attorney, Agent, or Firm* — Morgan, Lewis & Bockius LLP

(57) ABSTRACT

A measuring apparatus includes: a measuring unit to measure a signal value corresponding to a concentration of a specified substance contained in a first sample; an acquiring unit to acquire a reference value pertaining to the specified substance contained in a second sample; a calculation unit to calculate a concentration value of the specified substance contained in the first sample, based on the signal value and the reference value; a determination unit to determine whether a variation in the concentration value of the specified substance contained in the first sample is equal to or less than a threshold value; and an output unit to output, to a display unit, recommendation information representing recommendation for acquiring the reference value when the variation in the concentration value of the specified substance contained in the first sample is equal to or less than the threshold value.

18 Claims, 10 Drawing Sheets

(51) Int. Cl.
  *A61B 5/1495* (2006.01)
  *G16H 20/17* (2018.01)
  *G16H 10/40* (2018.01)
  *G01N 27/327* (2006.01)
  *G01N 33/487* (2006.01)
  *A61B 5/157* (2006.01)

(52) U.S. Cl.
  CPC ....... *A61B 5/4839* (2013.01); *G01N 27/3274* (2013.01); *G01N 33/4875* (2013.01); *G16H 10/40* (2018.01); *G16H 20/17* (2018.01); *A61B 5/157* (2013.01); *A61B 2560/0223* (2013.01)

(58) Field of Classification Search
  CPC .... A61B 5/14532; G16H 10/40; G16H 20/17; G01N 27/3274; G01N 33/4875
  See application file for complete search history.

(56) References Cited

U.S. PATENT DOCUMENTS

| | | | |
|---|---|---|---|
| 2005/0027180 A1* | 2/2005 | Goode, Jr. | A61B 5/1495 600/365 |
| 2008/0319295 A1 | 12/2008 | Bernstein et al. | |
| 2009/0006034 A1* | 1/2009 | Hayter | G06F 19/00 702/182 |
| 2010/0076284 A1 | 3/2010 | Bernstein et al. | |
| 2011/0029269 A1 | 2/2011 | Hayter et al. | |
| 2013/0109943 A1 | 5/2013 | Gottlieb et al. | |
| 2013/0113632 A1 | 5/2013 | Bernstein et al. | |
| 2013/0197847 A1 | 8/2013 | Tsukada et al. | |
| 2014/0088382 A1 | 3/2014 | Bernstein et al. | |

\* cited by examiner

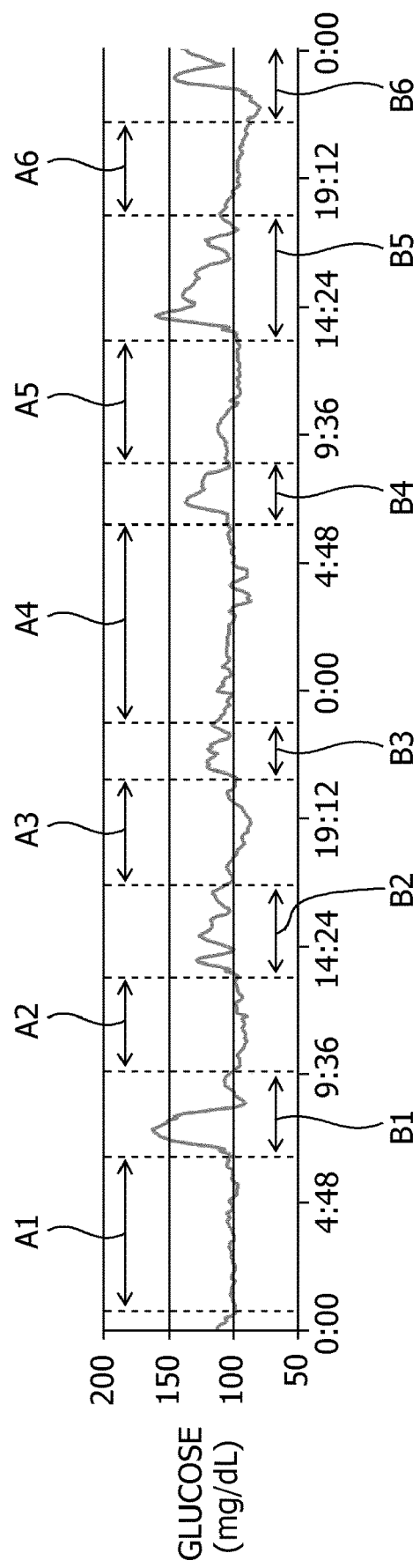

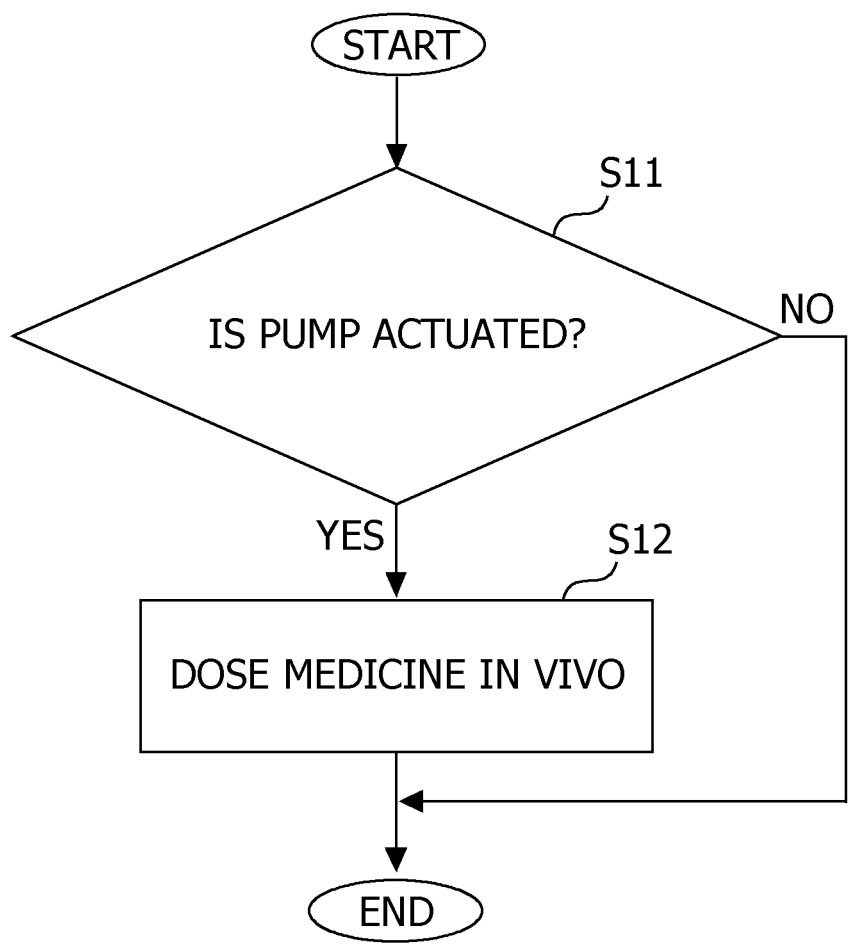

MEASURING APPARATUS, COMPUTER READABLE MEDIUM STORING MEASURING PROGRAM AND MEASURING METHOD

CROSS-REFERENCE TO RELATED APPLICATION

The present application claims priority to Japanese Patent Application No. 2017-131324, filed Jul. 4, 2017, and Japanese Patent Application No. 2018-123529, filed Jun. 28, 2018, the entire contents of which are incorporated herein by reference.

FIELD

An embodiment pertains to a measuring apparatus, a measuring program and a measuring method.

BACKGROUND

A variety of blood glucose level measuring apparatuses for measuring a self blood glucose level (a glucose concentration value in blood) are currently put on sale in the market. Known as the blood glucose level measuring apparatus are, e.g., a Self-Monitoring of Blood Glucose (SMBG) apparatus for self-monitoring (measuring) of the blood glucose and a Continuous Glucose Monitoring (CGM) apparatus for continuous glucose monitoring (measuring). The SMBG apparatus measures the blood glucose level in a way that attaches blood extracted from a finger tip by using a needling tool onto a test piece fitted to measurement equipment. The CGM apparatus continuously measures a glucose concentration in interstitial fluid by subcutaneously indwelling a micro sensor including electrodes and enzyme reacting to the glucose. The CGM apparatus consecutively measures the blood glucose level at an interval of several tens of seconds through several minutes by subcutaneously indwelling the sensor over a period as long as several days through several weeks.

In the CGM apparatus, a mode of retrospectively calculating (which will hereinafter be termed a retrospective mode) the glucose concentration value, is used by a health care professional for the purpose of obtaining a variation in glucose concentration value in a life style of a patient. Therefore, a specification for not causing the patient to be aware of the variation in blood glucose level is such that a display device is not provided in the CGM apparatus, or the glucose concentration value is not displayed on the display device. A divergence exists between the blood glucose level and the glucose concentration value. Consequently, the glucose concentration value in an interstitial fluid is made approximate to the blood glucose level by correcting the glucose concentration value in the interstitial fluid with reference to the inputted blood glucose level. Known is an analyte monitoring device for prospective or retrospective data analysis and processing (e.g., Patent document 1).
[Patent document 1] Japanese Patent No. 5680960

SUMMARY

Calibration of the CGM involves using the blood glucose level measured by the SMBG apparatus. However, a time lag exists between the blood glucose level and the glucose concentration value in the interstitial fluid, which is defined as a measurement target of the CGM. In other words, a fixed period of time is taken till the glucose concentration value in the interstitial fluid follows up the blood glucose level. Therefore, implementation of calibration of the CGM when the variation in blood glucose level is large, exerts an adverse influence on accuracy of a measurement value of the CGM apparatus as affected by the time lag.

The conventional technologies entail implementing the calibration of the CGM on the basis of the blood glucose level measured by the patient at arbitrary timing. Hence, the calibration of the CGM is implemented when causing the large variation in blood glucose level in some cases. It is feasible to avoid implementing the calibration of the CGM when there is the large variation in blood glucose level by displaying the glucose concentration value on the display device of the CGM. However, the retrospective mode entails not causing the patient to be aware of the variation in blood glucose level, and it is therefore unpreferable to display the glucose concentration value on the display device of the CGM. Even a real-time mode of displaying the glucose concentration value on the display device of the CGM also enables the health care professional to obtain the variation in glucose concentration value in the life style of the patient by not causing the patient to be aware of the variation in blood glucose level. However, the real-time mode has an apprehension that the calibration of the CGM is implemented when the variation in blood glucose level is large as in the case of the retrospective mode upon implementing the calibration of the CGM on the basis of the blood glucose level measured by the patient at the arbitrary timing. It is an object of the present invention, which is devised in view of such circumstances, to improve accuracy of measuring a concentration value of a specified substance in a sample.

According to an aspect of the embodiment, a measuring apparatus includes: a measuring unit configured to measure a signal value corresponding to a concentration of a specified substance contained in a first sample; an acquiring unit configured to acquire a reference value pertaining to the specified substance contained in a second sample; a calculation unit configured to calculate a concentration value of the specified substance contained in the first sample, based on the signal value and the reference value; a determination unit configured to determine whether a variation in the concentration value of the specified substance contained in the first sample is equal to or less than a threshold value; and an output unit configured to output, to a display unit, recommendation information representing recommendation for acquiring the reference value when the variation in the concentration value of the specified substance contained in the first sample is equal to or less than the threshold value.

According to the embodiment, it is feasible to improve the measurement accuracy of the concentration value of the specified substance in the sample.

BRIEF DESCRIPTION OF DRAWINGS

FIG. 4 is a chart illustrating a variation in glucose concentration value in an interstitial fluid;

FIG. 11 is a flowchart illustrating one example of a dose process in the dosage apparatus.

DESCRIPTION OF EMBODIMENT

Embodiments will hereinafter be described with reference to the drawings. The following embodiments are exemplifications, and the present invention is not limited to configurations of the embodiments given below.

In the measuring apparatus, the concentration value of the specified substance contained in the first sample is not displayed on the display unit. In the measuring apparatus, the output unit does not output the recommendation information to the display unit when the variation in the concentration value of the specified substance contained in the first sample is larger than the threshold value. In the measuring apparatus, the output unit outputs, to the display unit, non-recommendation information representing non-recommendation for acquiring the reference value when the variation in the concentration value of the specified substance contained in the first sample is larger than the threshold value.

According to an aspect of the embodiment, a measuring apparatus includes: a measuring unit configured to measure a signal value corresponding to a concentration of a specified substance contained in a first sample; an acquiring unit configured to acquire a reference value pertaining to the specified substance contained in a second sample; a calculation unit configured to calculate a concentration value of the specified substance contained in the first sample, based on the signal value and the reference value; a determination unit configured to determine whether a variation in the concentration value of the specified substance contained in the first sample is larger than a threshold value; and an output unit to output, to a display unit, non-recommendation information representing non-recommendation for acquiring the reference value when the variation in the concentration value of the specified substance contained in the first sample is larger than the threshold value.

In the measuring apparatus, the concentration value of the specified substance contained in the first sample is not displayed on the display unit. In the measuring apparatus, the output unit does not output the non-recommendation information to the display unit when the variation in the concentration value of the specified substance contained in the first sample is equal to or less than the threshold value.

The aspect described above may be attained in a way that causes a program to be run by a computer. To be specific, the aspect described above may be specified as a program to be run by the computer, or as a computer readable recording medium on which the program is recorded. The aspect described above may also be specified as a method executed by the computer. The aspect described above may further be specified as a system including the measuring apparatus.

First Embodiment

Figure 1:
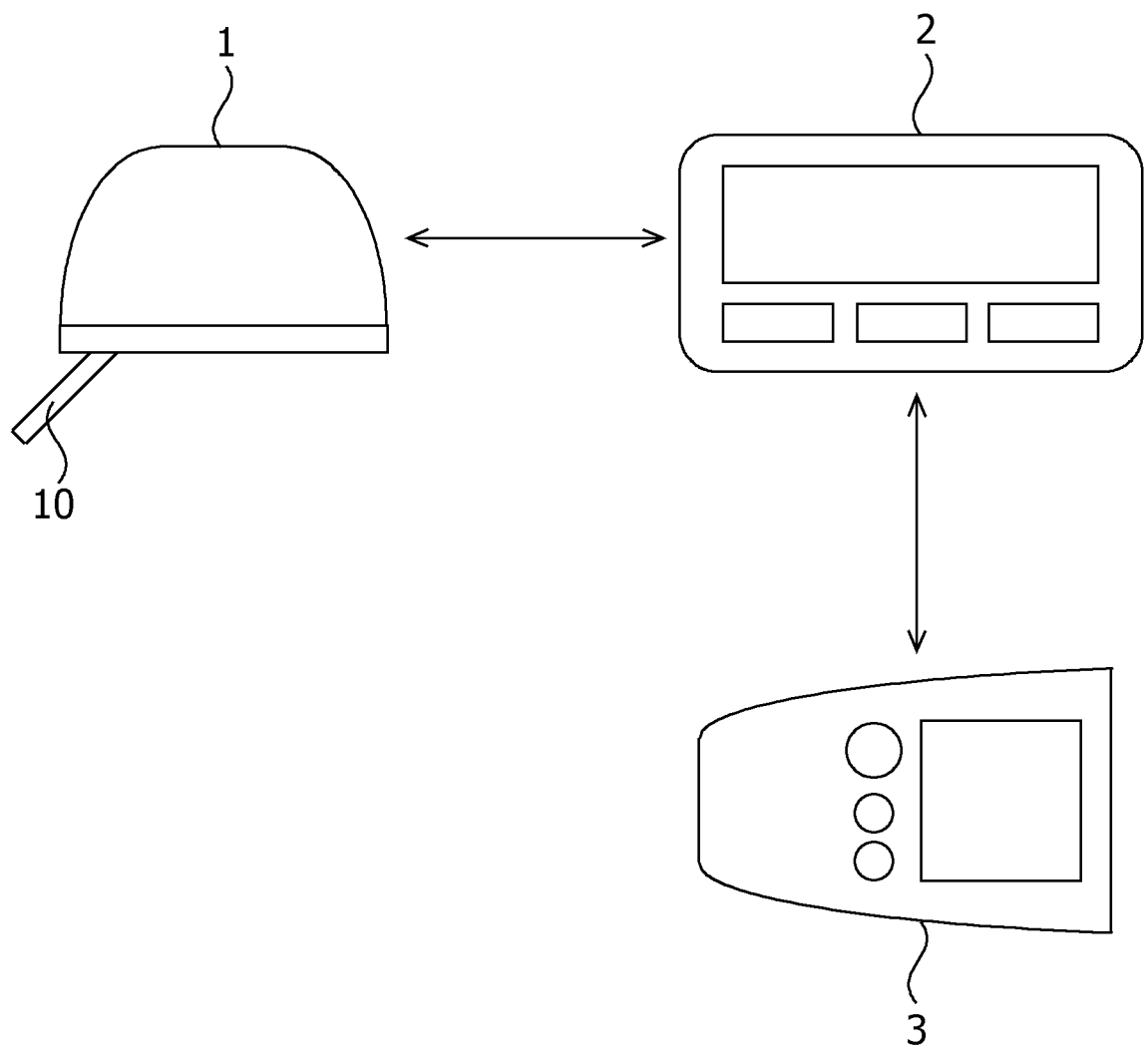
FIG. 1 is a view of a configuration of a measuring system according to a first embodiment.

FIG. 1 is a diagram of a configuration of a measuring system according to a first embodiment. The measuring system illustrated in FIG. 1 includes a transmitting apparatus 1, a receiving apparatus 2 and a detection apparatus 3. The transmitting apparatus 1 consecutively measures a concentration of a specified substance (measurement target substance) in a first sample in vivo, and transmits a measurement result to the receiving apparatus 2. The transmitting apparatus 1 may be used by being attached to regions instanced by a brachial region, an abdominal region and a gluteal region of a user (patient). The transmitting apparatus 1 may also be a Continuous Glucose Monitoring (CGM) apparatus for performing continuous glucose monitoring (measurement). A body fluid instanced by an interstitial fluid is given as the first sample in vivo. The specified substance is exemplified by glucose contained in the interstitial fluid. The specified substance may also be a substance other than glucose.

The receiving apparatus 2 receives a measurement result from the transmitting apparatus 1. The receiving apparatus 2 performs wireless data communications with the transmitting apparatus 1, and also performs the wireless data communications with the detection apparatus 3. The receiving apparatus 2 may perform wired data communications with the transmitting apparatus 1, and may also perform the wired data communications with the detection apparatus 3. The transmitting apparatus 1 and the receiving apparatus 2 are configured as separate equipments in the first embodiment, and may also be configured integrally.

The detection apparatus 3 is an apparatus to measure a concentration of the specified substance in a second sample extracted in vitro. A body fluid instanced by blood is given as the second sample extracted in vitro. The detection apparatus 3 may also be a Self-Monitoring of Blood Glucose (SMBG) apparatus for conducting self-monitoring of blood glucose. The detection apparatus 3 measures a current value corresponding to a glucose concentration in the blood. The detection apparatus 3 converts the current value into a glucose concentration value in the blood with reference to calibration curve data, thereby measuring the glucose concentration value in the blood. The current value and the glucose concentration value in the blood, which are measured by the detection apparatus 3, are transmitted and inputted to the receiving apparatus 2.

<Transmitting Apparatus>

The transmitting apparatus 1 includes a sensor 10 is used by being implanted into a subcutaneous region of the user. The transmitting apparatus 1 is pasted to a skin of the user by an adhesive tape and other equivalent materials, or is attached to a belt and other equivalent articles, thereby being fitted to the user. The sensor 10 is an electrochemical sensor that measures a specified component (e.g., a concentration of the specified substance) in the sample by utilizing electrochemical reaction. The sensor 10 is indwelled subcutaneously over a consecutive measurement period as long as, e.g., several days through several weeks, and the transmitting apparatus 1 consecutively measures the glucose concentration in the interstitial fluid. "Being consecutive" connotes that the transmitting apparatus 1 continuously measures the glucose concentration in a state of the sensor 10 being subcutaneously indwelled, and encompasses such a mode that the transmitting apparatus 1 measures the glucose concentration at an interval of predetermined time. A measurement frequency of the glucose concentration may be arbitrarily set with respect to the transmitting apparatus 1. For example, the measurement frequency of the glucose concentration may also be set with respect to the transmitting apparatus 1 so that the transmitting apparatus 1 measures the glucose concentration at a frequency of once every several ten seconds through several minutes.

Figure 2:
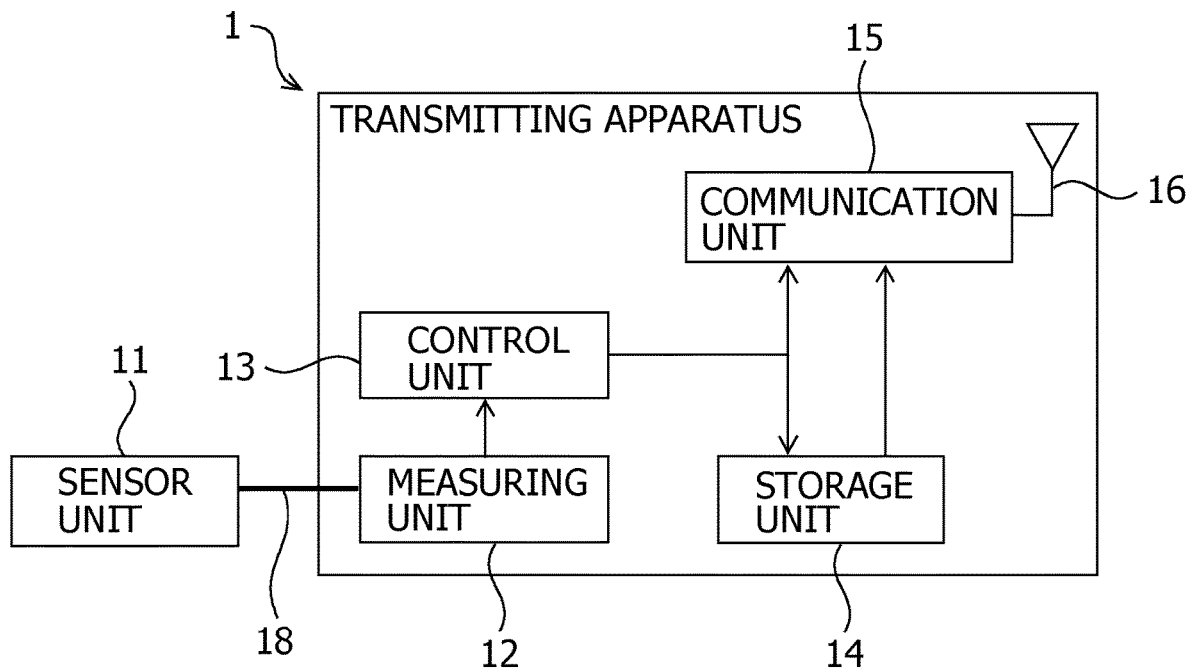
FIG. 2 is a block diagram of a configuration of a measuring apparatus according to the first embodiment.

FIG. 2 is a block diagram of a configuration of the transmitting apparatus 1 according to the first embodiment. The transmitting apparatus 1 is a transmitter that transmits various items of data to the receiving apparatus 2. The transmitting apparatus 1 includes a sensor unit 11, a measurement unit 12, a control unit (arithmetic unit) 13, a storage unit 14, a communication unit 15 and an antenna 16. The sensor unit 11 has glucose oxidoreductase instanced by glucose oxidase (GOD) and glucose dehydrogenase (GDH), and a plurality of electrodes, i.e., a working electrode, a counter electrode, a reference electrode and other equivalent electrodes. The sensor unit 11 is provided on the side of a tip of the sensor 10 illustrated in FIG. 1. The sensor unit 11 is electrically connected to the measurement unit 12 via a wire 17.

The measurement unit 12 is a circuit to measure a signal value (e.g., a response current value) by applying a voltage to the sensor unit 11. When the voltage is applied to between the electrodes (between the working electrode and the counter electrode, or between the working electrode and the reference electrode) of the sensor unit 11, the sensor unit 11 outputs a response current value corresponding to the glucose concentration in the body fluid. The measurement unit 12 measures the response current value outputted from the sensor unit 11 in a way that controls the voltage to be applied to between the electrodes of the sensor unit 11. When the voltage is applied to between the electrodes of the sensor unit 11, the glucose in the body fluid is oxidized by the oxidoreductase, and electrons being thereby extracted are supplied to the working electrode. The measurement unit 12 measures, as the response current value, a quantity of electric charges of the electrons supplied to the working electrode. The measurement unit 12 may convert the response current value into a response voltage value, and may measure, as the response voltage value, the quantity of electric charges of the electrons supplied to the working electrode. The following discussion will deal with a case that the measurement unit 12 measures the response current value. The response current value measured by the measurement unit 12 is sent to the control unit 13.

The control unit 13 controls the measurement unit 12, the storage unit 14 and the communication unit 15. The control unit 13, the storage unit 14 and the communication unit 15 may be attained by: computers each including a Central Processing Unit (CPU), a Random Access Memory (RAM), a Read Only Memory (ROM) and other equivalent hardware components that are provided in the transmitting apparatus 1; respective apparatuses; and programs and other equivalent software components running on the computer. The CPU is also called a processor. It does not mean that the CPU is limited to the single processor, and the CPU may, however, take a multi-processor configuration.

The control unit 13 stores the response current value in the storage unit 14, and sends the response current value to the communication unit 15. The communication unit 15 transmits the response current value to the receiving apparatus 2 via the antenna 16. The communication unit 15 may send the response current value transmitted from the control unit 13 to the receiving apparatus 2, and may also send the response current value stored in the storage unit 14 to the receiving apparatus 2.

<Receiving Apparatus>

Figure 3:
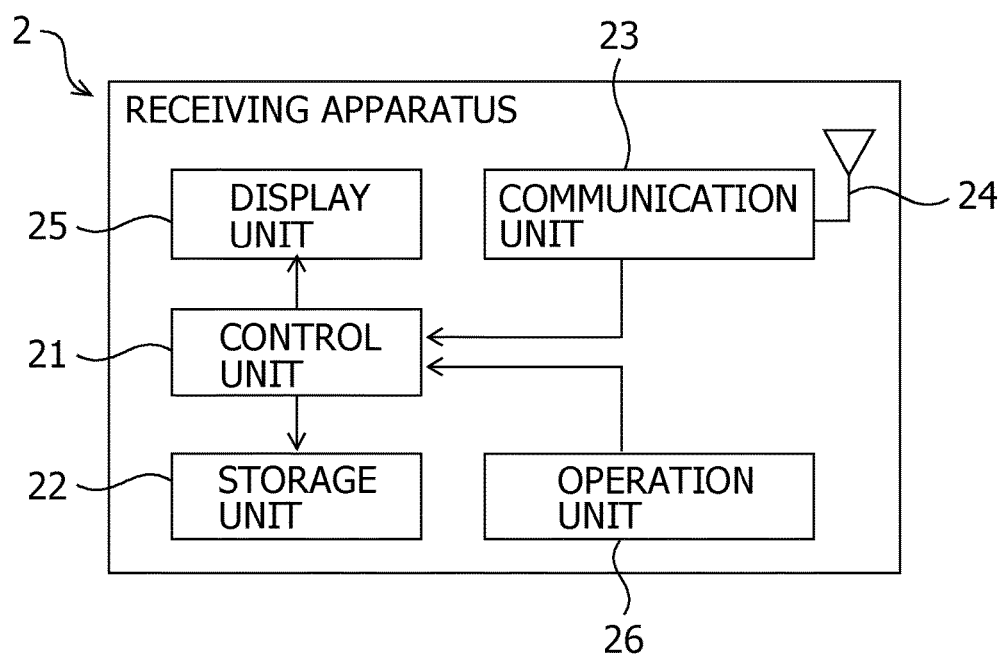
FIG. 3 is a block diagram of a configuration of a receiving apparatus according to the first embodiment.

FIG. 3 is a block diagram illustrating a configuration of the receiving apparatus 2 according to the first embodiment. The receiving apparatus 2 receives the various items of data from the transmitting apparatus 1, and displays the received data. The receiving apparatus 2 includes a control unit (arithmetic unit) 21, a storage unit 22, a communication unit 23, an antenna 24, a display unit 25, and an operation unit 26. The control unit 21 controls the storage unit 22, the communication unit 23, and the display unit 25. The control unit 21, the storage unit 22, and the communication unit 23 may be attained by: computers each including the CPU, the RAM, the ROM and other equivalent hardware components that are provided in the receiving apparatus 2; respective apparatuses; and programs and other equivalent software components running on the computer.

The display unit 25 has a display and displays various types of information and messages on this display. The display unit 25 displays a measurement result and an error on the display, and also displays operation procedures, operation statuses and other equivalent items when setting is done. The display of the display unit 25 is exemplified by a liquid crystal display apparatus, a plasma display panel, a Cathode Ray Tube (CRT) display, or an Electroluminescence (EL) panel. The display unit 25 may have a voice output unit to output voices and sounds. The operation unit 26 includes a variety of operation buttons, a touch panel and other equivalent components, and accepts the various types of information from the user.

The communication unit 23 receives the response current value from the transmitting apparatus 1 via the antenna 24, and sends the received response current value to the control unit 21. The control unit 21 stores the received response current value in the storage unit 22. The control unit 21 converts the response current value into the glucose concentration value with reference to calibration curve data stored in the storage unit 22. The calibration curve data indicating a correspondence relation between the response current value and the glucose concentration in the interstitial fluid is pre-stored in the storage unit 22. The calibration curve data is pre-stored as, e.g., a mathematical expression and a correspondence table in the storage unit 22. The control unit 21 is one example of a "measuring unit".

The communication unit 23 receives a reference value pertaining to the glucose in the blood (which will hereinafter be referred to as a glucose reference value) from the detection apparatus 3 via the antenna 24, and sends the received glucose reference value to the control unit 21. The control unit 21 acquires and stores the glucose reference value in the storage unit 22. The control unit 21 is one example of an "acquiring unit". The control unit 21 corrects the glucose concentration value in the interstitial fluid by using the glucose reference value. The glucose concentration value in the blood is not coincident with the glucose concentration value in the interstitial fluid. Therefore, the control unit 21 corrects the glucose concentration value in the interstitial fluid by use of the glucose reference value, thereby executing a process of making the glucose concentration value in the interstitial fluid approximate to the glucose concentration value in the blood.

The glucose reference value is, e.g., the glucose concentration value in the blood. The control unit 21 may calculate the glucose concentration value in the interstitial fluid on the basis of the response current value, and may correct the glucose concentration value in the interstitial fluid with reference to the in-blood glucose concentration value measured by the detection apparatus 3. The glucose concentration value in the interstitial fluid, which is corrected with reference to the in-blood glucose concentration value measured by the detection apparatus 3, will hereinafter be termed a post-correcting glucose concentration value. The glucose concentration value may also be the current value measured by the detection apparatus 3. The control unit 21 may correct the response current value with reference to the current value measured by the detection apparatus 3, and may also calculate the glucose concentration value in the interstitial fluid on the basis of the post-correcting response current value. The glucose concentration value in the interstitial fluid, which is calculated based on the post-correcting response current value, will hereinafter be termed the post-correcting glucose concentration value. The control unit 21 is one example of a "calculation unit".

<First Determination Process>

A first determination process will be described. The control unit 21 determines whether a variation in glucose concentration value in the interstitial fluid is equal to or less than a threshold value. The variation in glucose concentration value in the interstitial fluid is, e.g., a difference between a maximum value and a minimum value of the glucose concentration value in the interstitial fluid per unit time. When each of the glucose concentration values in the interstitial fluid, which are measured a plural number of times, falls within a range of a predetermined concentration value, the control unit 21 may determine that the variation in glucose concentration value in the interstitial fluid is equal to or less than the threshold value. When the glucose concentration value in the interstitial fluid falls within a range of +10% through −10% of the predetermined concentration value, the control unit 21 may determine that the variation in glucose concentration value in the interstitial fluid is equal to or less than the threshold value. The control unit 21 is one example of a "determination unit".

FIG. 4 is a chart illustrating the variation in glucose concentration value in the interstitial fluid. In FIG. 4, an axis of ordinate represents the glucose concentration value (mg/dL) in the interstitial fluid, while an axis of abscissa represents time. The variation in glucose concentration value in the interstitial fluid is small for each of periods A1-A6 in FIG. 4. For example, the control unit 21 determines that the variation in glucose concentration value in the interstitial fluid for each of the periods A1-A6 in FIG. 4 is equal to or less than the threshold value. The variation in glucose concentration value in the interstitial fluid is large for each of periods B1-B6 in FIG. 4. For instance, the control unit 21 determines that the variation in glucose concentration value in the interstitial fluid for each of the periods B1-B6 in FIG. 4 is larger than the threshold value.

When the variation in glucose concentration value in the interstitial fluid is equal to or less than the threshold value, the control unit 21 outputs recommendation information to the display unit 25, and the display unit 25 displays the recommendation information. The recommendation information is information instanced by an emoticons (pictograph), a graphic form, a color and a text (message) each representing recommendation for acquiring the glucose concentration value in the blood. The emoticons, the graphic form, the text and other equivalent elements each representing the recommendation for acquiring the glucose concentration value in the blood, may be colored. For example, for the periods A1-A6 in FIG. 4, the control unit 21 outputs the recommendation information to the display unit 25, and the display unit 25 displays the recommendation information. When the variation in glucose concentration value in the interstitial fluid is equal to or less than the threshold value, the control unit 21 may output request information to the display unit 25, and the display unit 25 may also display the request information. The request information is information instanced by an emoticons, a graphic form, a color and a text each representing a request for acquiring the glucose concentration value in the blood. The emoticons, the graphic form, the color and the text each representing the request for acquiring the glucose concentration value in the blood, may be colored. The control unit 21 is one example of an "output unit".

When the variation in glucose concentration value in the interstitial fluid is larger than the threshold value, the control unit 21 does not output the recommendation information to the display unit 25, and the display unit 25 does not display the recommendation information. For instance, for each of the periods B1-B6 in FIG. 4, the control unit 21 does not output the recommendation information to the display unit 25, and the display unit 25 does not display the recommendation information. When the variation in glucose concentration value in the interstitial fluid is larger than the threshold value, the control unit 21 does not output the request information to the display unit 25, and the display unit 25 does not display the request information. The variation in glucose concentration value in the interstitial fluid is larger than the threshold value, in which case the control unit 21 may output non-recommendation information to the display unit 25, and the display unit 25 may display the non-recommendation information. The non-recommendation information is information instanced by an emoticons, a graphic form, a color and a text each representing that the acquisition of the glucose concentration value in the blood is not recommended. The emoticons, the graphic form, the text and other equivalent elements each representing that the acquisition of the glucose concentration value in the blood is not recommended, may be colored. For example, for each of the periods B1-B6, the control unit 21 outputs the non-recommendation information to the display unit 25, and the display unit 25 displays the non-recommendation information.

Figure 5A:
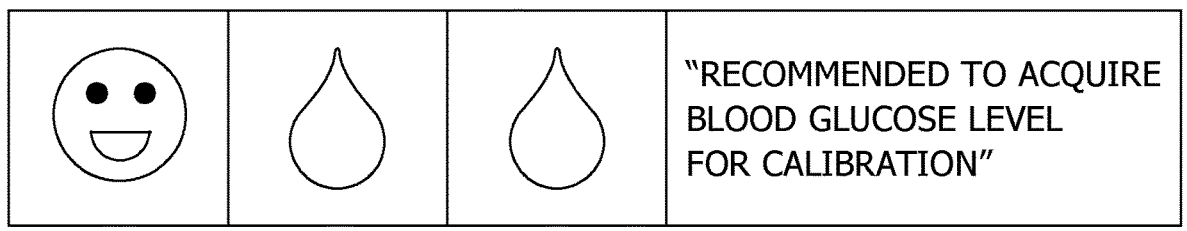
FIG. 5A is a diagram illustrating one example of recommendation information.

FIG. 5A is a diagram illustrating one example of the recommendation information. One example of the emoticons representing that the acquisition of the glucose concentration value in the blood is recommended, is depicted in a first field counted from left in FIG. 5A. One example of the graphic form representing that the acquisition of the glucose concentration value in the blood is recommended, is depicted in a second field counted from the left in FIG. 5A. A color (white) representing that the acquisition of the glucose concentration value in the blood is recommended, is depicted in a second field counted from right in FIG. 5A. A text representing that the acquisition of the glucose concentration value in the blood is recommended, is depicted in a first field counted from the right in FIG. 5A.

Figure 5B:
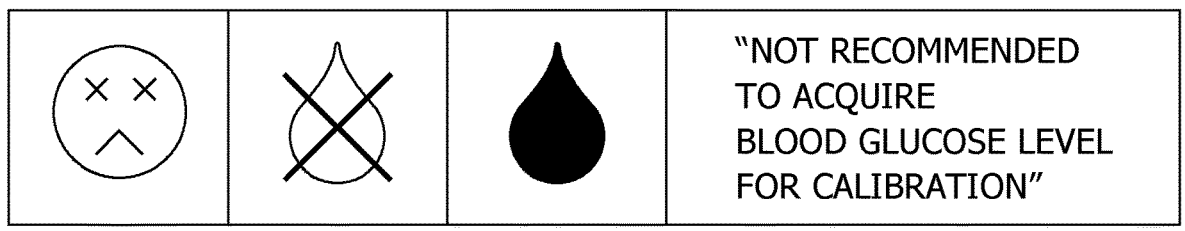
FIG. 5B is a diagram illustrating one example of non-recommendation information.

FIG. 5B is a diagram illustrating one example of the non-recommendation information. One example of the emoticons representing that the acquisition of the glucose concentration value in the blood is not recommended, is depicted in a first field counted from the left in FIG. 5B. One example of the graphic form representing that the acquisition of the glucose concentration value in the blood is not recommended, is depicted in a second field counted from the left in FIG. 5B. A color (black) representing that the acquisition of the glucose concentration value in the blood is not recommended, is depicted in a second field counted from the right in FIG. 5B. A text representing that the acquisition of the glucose concentration value in the blood is not recommended, is depicted in a first field counted from the right in FIG. 5B.

Figure 6A:
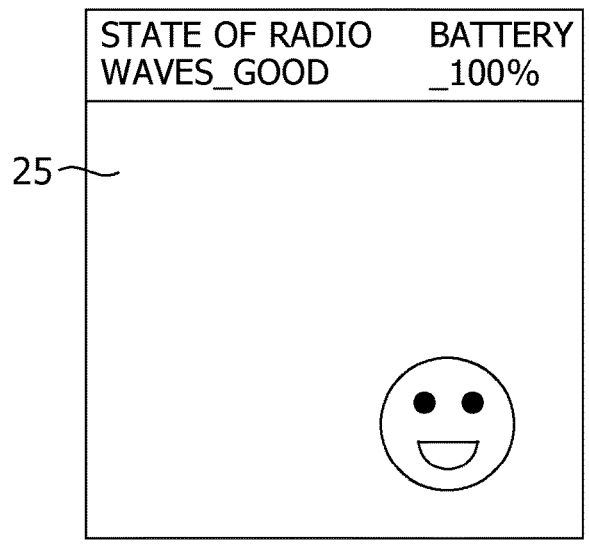
FIGS. 6A and 6B are diagrams each illustrating one example of the recommendation information displayed on a display unit.
Figure 6B:
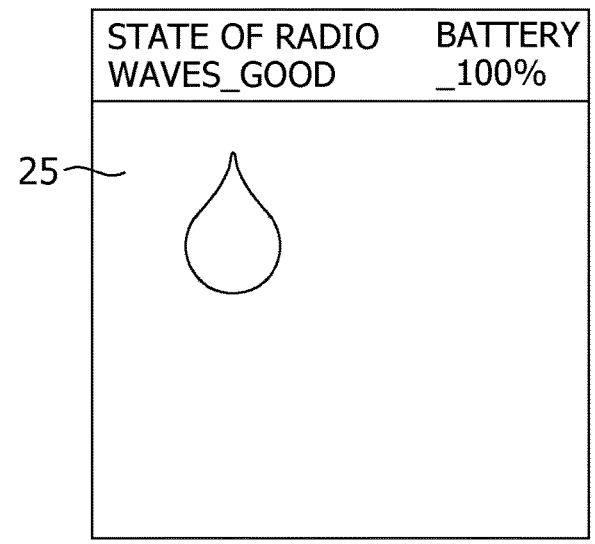
Figure 6C:
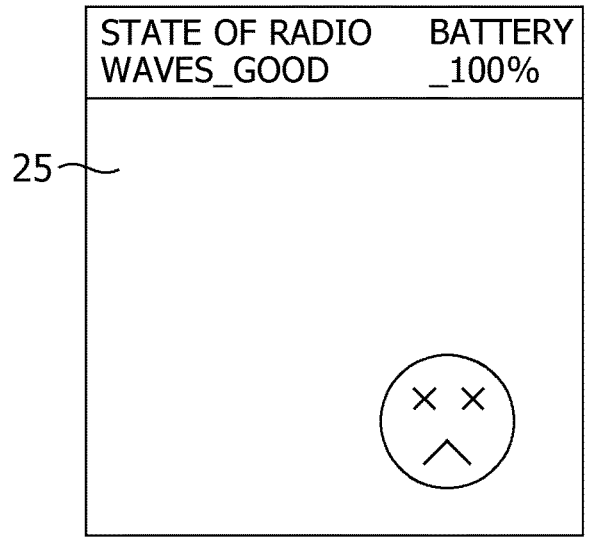
FIGS. 6C and 6D are diagrams each illustrating one example of non-recommendation information displayed on the display unit.
Figure 6D:
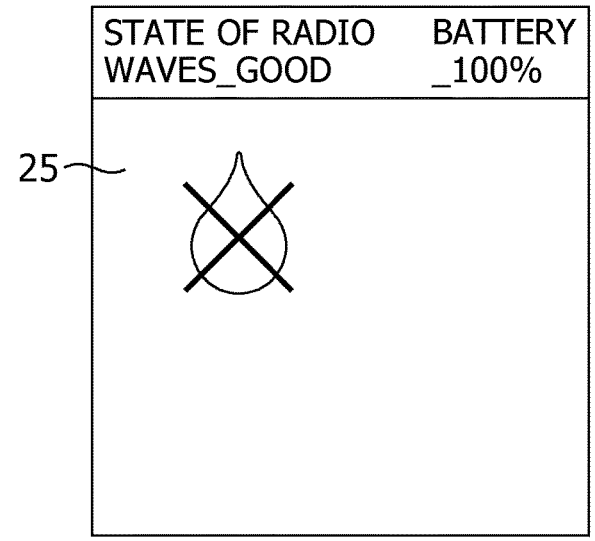

FIGS. 6A and 6B are diagrams each illustrating one example of the recommendation information displayed on the display unit 25. As depicted in FIG. 6A, the emoticons representing that the acquisition of the glucose concentration value in the blood is recommended, is displayed on the display unit 25. As depicted in FIG. 6B, the graphic form representing that the acquisition of the glucose concentration value in the blood is recommended, is displayed on the display unit 25. FIGS. 6C and 6D are diagrams each illustrating one example of the non-recommendation information displayed on the display unit 25. As depicted in FIG. 6C, the emoticons representing that the acquisition of the glucose concentration value in the blood is not recommended, is displayed on the display unit 25. As depicted in FIG. 6D, the graphic form representing that the acquisition of the glucose concentration value in the blood is not recommended, is displayed on the display unit 25.

For example, the recommendation information illustrated in FIG. 6A may be displayed on the display unit 25 for each of the periods A1-A6 in FIG. 4, and the non-recommendation information depicted in FIG. 6C may be displayed on the display unit 25 for each of the periods B1-B6 in FIG. 4. For instance, the recommendation information depicted in FIG. 6B may be displayed on the display unit 25 for each of the periods A1-A6 in FIG. 4, and the non-recommendation information depicted in FIG. 6C may be displayed on the display unit 25 for each of the periods B1-B6 in FIG. 4.

When the recommendation information or the request information is displayed on the display unit 25, the user measures the glucose concentration in the blood by using the detection apparatus 3. Accordingly the recommendation information is information for recommending the user to measure the glucose concentration in the blood by use of the detection apparatus 3. The request information is information for requesting the user to measure the glucose concentration in the blood by using the detection apparatus 3. The current value or the glucose concentration value in the blood, which is measured by the detection apparatus 3, is sent to and inputted to the receiving apparatus 2. The control unit 21 calibrates the glucose reference value by updating the glucose reference value pre-stored in the storage unit 22, based on the current value or the glucose concentration value in the blood inputted to the receiving apparatus 2.

The control unit 21 does not output the glucose concentration value in the interstitial fluid, the variation in glucose concentration value in the interstitial fluid and the glucose concentration value in the blood to the display unit 25. The display unit 25 does not therefore display the glucose concentration value in the interstitial fluid, the variation in glucose concentration value in the interstitial fluid and the glucose concentration value in the blood.

A time lag exists between the glucose concentration value in the blood and the glucose concentration value in the interstitial fluid. In other words, a fixed period of time is taken till the glucose concentration value in the interstitial fluid follows up the glucose concentration value in the blood. For example, even when there is a large variation in glucose concentration value in the interstitial fluid, a variation in glucose concentration value in the blood is small as the case may be. Such a possibility exists that the post-correcting glucose concentration value diverges largely from the glucose concentration value in the blood upon calibrating the glucose reference value when there is a large variation in glucose concentration value in the interstitial fluid. When the variation in glucose concentration value in the interstitial fluid is equal to or less than the threshold value, the control unit 21 outputs the recommendation information to the display unit 25, and the display unit 25 displays the recommendation information. The user visually recognizes the recommendation information displayed on the display unit 25, and measures the glucose concentration in the blood by using the detection apparatus 3, thereby restraining the divergence between the post-correcting glucose concentration value and the glucose concentration value in the blood. This leads to the improvement of the measurement accuracy of the glucose concentration value in the interstitial fluid.

<Second Determination Process>

A second determination process will be described. The control unit 21 determines whether the variation in glucose concentration value in the interstitial fluid is larger than the threshold value. When the variation in glucose concentration value in the interstitial fluid is larger than the threshold value, the control unit 21 outputs the non-recommendation information to the display unit 25, and the display unit 25 displays the non-recommendation information. When the variation in glucose concentration value in the interstitial fluid is larger than the threshold value, the control unit 21 does not output the recommendation information to the display unit 25, and the display unit 25 does not display the recommendation information. Whereas when the variation in glucose concentration value in the interstitial fluid is equal to or less than the threshold value, the control unit 21 does not output the recommendation information, the request information and the non-recommendation information to the display unit 25, and the display unit 25 does not display the recommendation information, the request information and the non-recommendation information.

When the non-recommendation information is not displayed on the display unit 25, the user measures the glucose concentration in the blood by employing the detection apparatus 3. The current value or the in-blood glucose concentration value measured by the detection apparatus 3 is sent to and inputted to the receiving apparatus 2. The control unit 21 calibrates the glucose reference value by updating the glucose reference value pre-stored in the storage unit 22, based on the current value or the in-blood glucose concentration value inputted to the receiving apparatus 2.

The control unit 21 does not output the glucose concentration value in the interstitial fluid, the variation in glucose concentration value in the interstitial fluid and the glucose concentration value in the blood to the display unit 25. Hence, the display unit 25 does not display the glucose concentration value in the interstitial fluid, the variation in glucose concentration value in the interstitial fluid and the glucose concentration value in the blood. When the glucose concentration value in the interstitial fluid is larger than the threshold value, the control unit 21 outputs the non-recommendation information to the display unit 25, and the display unit 25 displays the non-recommendation information. The user recognizes that the non-recommendation information is not displayed on the display unit 25, and measures the glucose concentration in the blood by using the detection apparatus 3, thereby restraining the divergence between the post-correcting glucose concentration value and the glucose concentration value in the blood. This leads to the improvement of the measurement accuracy of the glucose concentration value in the interstitial fluid.

A retrospective mode may be set in the receiving apparatus 2. When the retrospective mode is set in the receiving apparatus 2, neither the glucose concentration value in the interstitial fluid, nor the variation in glucose concentration value in the interstitial fluid, nor the glucose concentration value in the blood is displayed on the display unit 25. The user is thereby enabled to measure the glucose concentration in the blood by employing the detection apparatus 3 without being aware of the variation in glucose concentration value in the blood. As a result, it is feasible to improve the measurement accuracy of the glucose concentration value in the interstitial fluid without causing any decline of a utility value as the retrospective mode set in the receiving apparatus 2. A real mode (normal mode) may be set in the receiving apparatus 2. When the real mode is set in the receiving apparatus 2, at least one of the glucose concentration value in the interstitial fluid, the variation in glucose concentration value in the interstitial fluid and the glucose concentration value in the blood is displayed on the display unit 25.

It is preferable that the glucose reference value is calibrated once or several times per day in terms of considering the divergence between the glucose concentration value in the blood and the glucose concentration value in the interstitial fluid. When a period of elapse time since calibrating the glucose reference value is equal to or longer than a predetermined period of time, the control unit 21 may determine whether the variation in glucose concentration value in the interstitial fluid is equal to or less than the threshold value. The predetermined period of time is exemplified by 24 hours, 12 hours, 8 hours and 6 hours by way of one example.

<Detection Apparatus>

Figure 7:
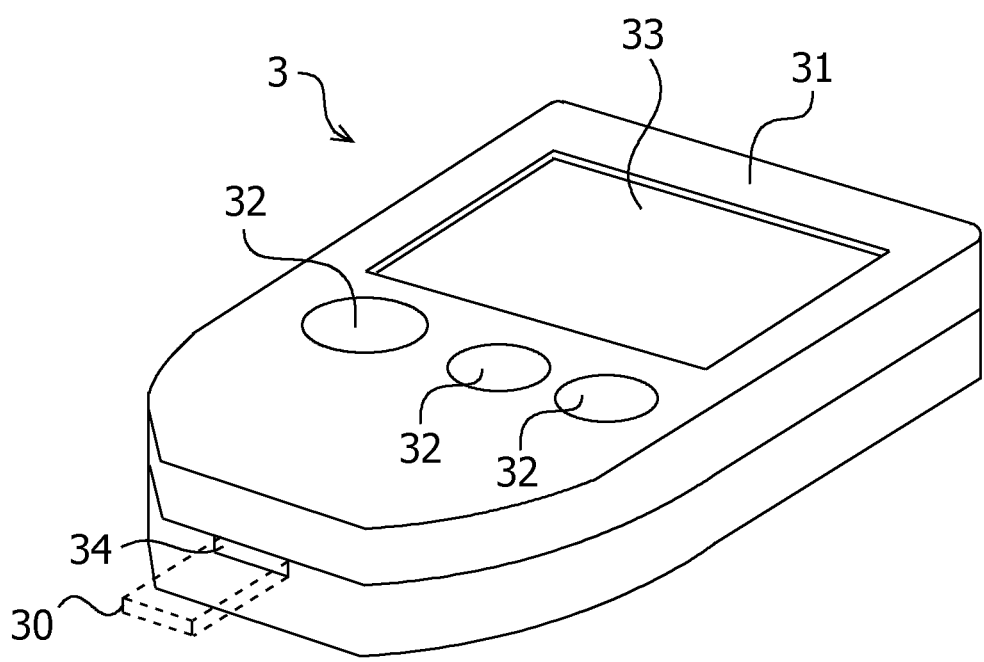
FIG. 7 is a schematic view of a configuration of a detection apparatus according to the first embodiment.

FIG. 7 is a schematic view illustrating a configuration of the detection apparatus 3 according to the first embodiment. The detection apparatus 3 measures the glucose concentration in the blood by an electrochemical method using the biosensor 30. The detection apparatus 3 includes a housing 31, a plurality of operation buttons 32, a display panel 33 and a sensor insertion port 34. The detection apparatus 3 further includes, though not illustrated, a circuit board mounted with electronic components, i.e., a circuit, a CPU, a RAM, a ROM and other components that are required for predetermined operations (instanced by applying the voltage or performing communications with the outside) of the detection apparatus 3.

As depicted in FIG. 7, the housing 31 is provided with the operation buttons 32 and a display panel 33. The operation buttons 32 are employed for making various settings (setting of measurement conditions, inputting of user's ID and other equivalent settings), and for conducting operations to start and finish the measurement. The operation buttons 32 may also be a contact type touch panel. The display panel 33 displays the measurement result and the error, and further displays the operation procedures, the operation statuses and other equivalent items when setting is done. The display panel 33 is exemplified by the liquid crystal display apparatus, the plasma display panel, the CRT display, or the Electroluminescence panel. The operation buttons 32 may be integral with the display panel 33.

The biosensor 30 includes a substrate, a plurality of electrodes, i.e., the working electrode, the counter electrode and the reference electrode each provided on the substrate, and the glucose oxidoreductase. A capillary is formed inside of the biosensor 30. The capillary of the biosensor 30 is provided with a reagent layer, and retains the blood. The biosensor 30 is inserted into the sensor insertion port 34. The detection apparatus 3 applies a voltage to between the electrodes of the biosensor 30, and thus measures a signal value (e.g., the current value). When the voltage is applied to between the electrodes of the biosensor 30, the biosensor 30 outputs the response current value corresponding to the glucose concentration in the blood.

The detection apparatus 3 measures the response current value outputted from the biosensor 30 in a way that controls the voltage applied to between the electrodes of the biosensor 30. When the voltage is applied to between the electrodes of the biosensor 30, the glucose in the blood is oxidized by the glucose oxidoreductase, and the electrons being thereby extracted are supplied to the working electrode. The detection apparatus 3 measures, as the current value, the quantity of electric charges of the electrons supplied to the working electrode. The detection apparatus 3 may convert the current value into the voltage value, and may measure, as the voltage value, the quantity of electric charges of the electrons supplied to the working electrode. The first embodiment will discuss a case that the detection apparatus 3 measures the current value.

Figure 8:
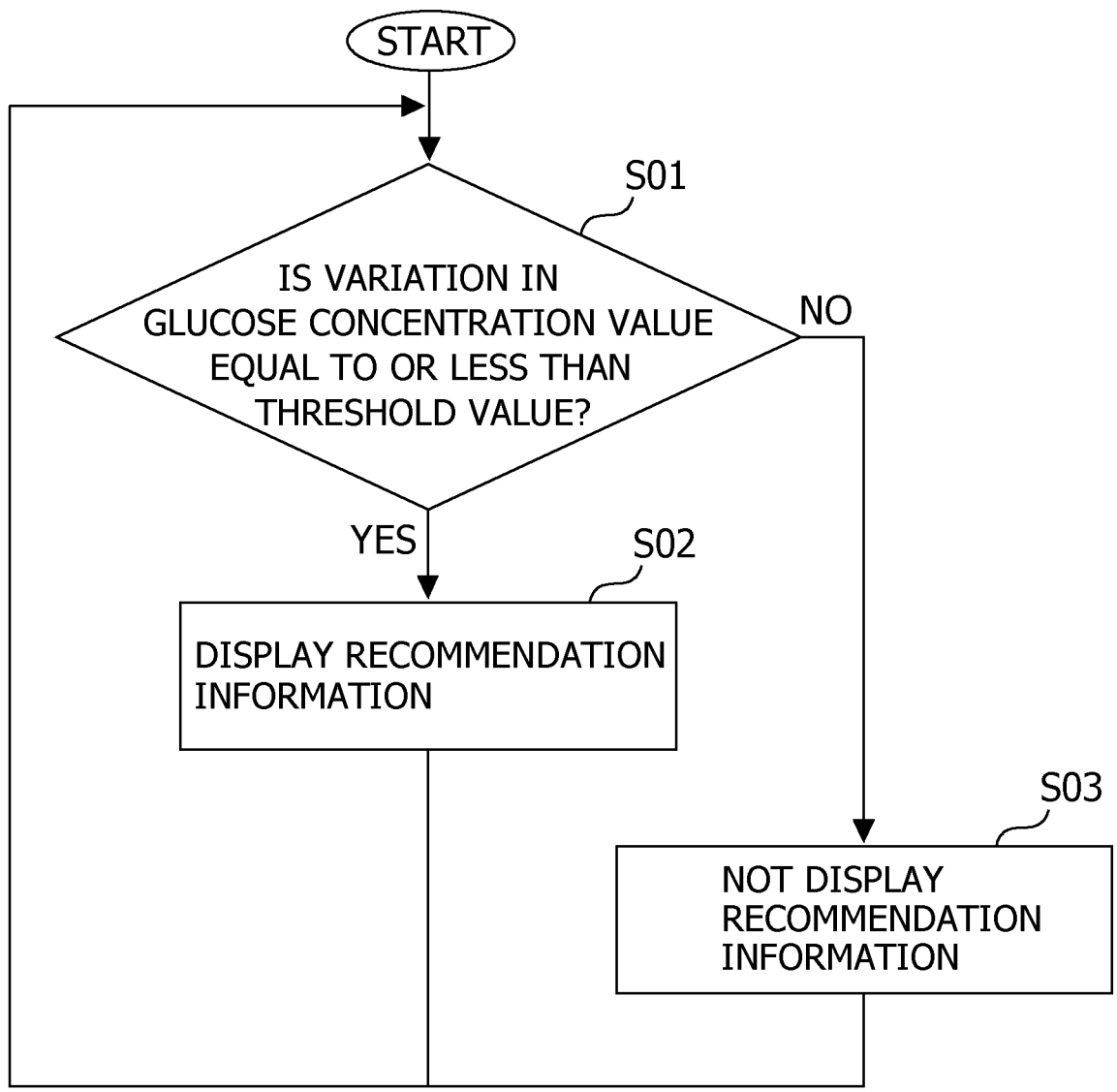
FIG. 8 is a flowchart illustrating one example of a display process in the receiving apparatus.

FIG. 8 is a flowchart illustrating one example of a display process in the receiving apparatus 2. After switching ON a power source of the transmitting apparatus 1 and then switching ON a power source of the receiving apparatus 2, the transmitting apparatus 1 is fitted to a body surface of the user and is thus attached to the user. A start of the flow illustrated in FIG. 8 is triggered by initializing the transmitting apparatus 1 and then initializing the receiving apparatus 2. The flowchart illustrated in FIG. 8 is an explanatory chart in the case of the first determination process.

In step S01, the control unit 21 determines whether the variation in glucose concentration value in the interstitial fluid is equal to or less than the threshold value. When the variation in glucose concentration value in the interstitial fluid is equal to or less than the threshold value, the processing proceeds to step S02. Whereas when the variation in glucose concentration value in the interstitial fluid is larger than the threshold value, the processing diverts to step S03.

In step S02, the control unit 21 outputs the recommendation information to the display unit 25, and the display unit 25 displays the recommendation information. In step S02, the control unit 21 may output the request information to the display unit 25, and the display unit 25 may display the request information.

In step S03, the control unit 21 does not output the recommendation information to the display unit 25, and the display unit 25 does not display the recommendation information. In step S03, the control unit 21 does not output the request information to the display unit 25, and the display unit 25 does not display the request information. In step S03, the control unit 21 may output the non-recommendation information to the display unit 25, and the display unit 25 may display the non-recommendation information.

Note that the control unit 21 does not output the recommendation information and the request information to the display unit 25, and the display unit 25 does not display the recommendation information and the request information in step S02 in the case of the second determination process. The control unit 21 outputs the non-recommendation information to the display unit 25 without outputting the recommendation information and the request information to the display unit 25 in step S03 in the case of the second determination process. The display unit 25 displays the non-recommendation information in step S03 in the case of the second determination process.

Second Embodiment

A second embodiment will be described. The following discussion will be focused on different points between the first embodiment and the second embodiment, and the same components in the second embodiment as those in the first embodiment are marked with the same numerals and symbols as those in the first embodiment, while their repetitive explanations are omitted.

Figure 9:
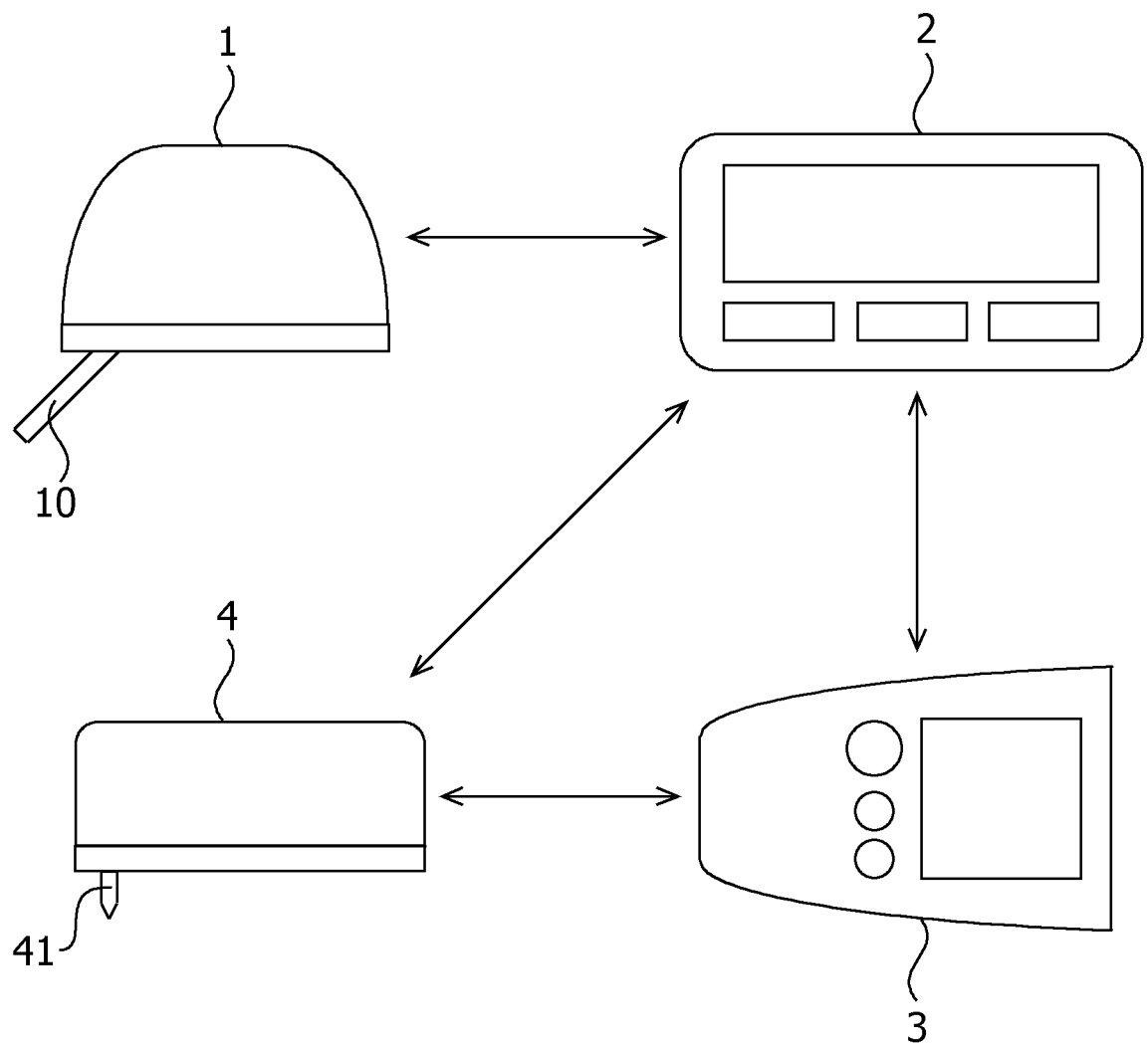
FIG. 9 is a view of a configuration of a measuring system according to a second embodiment.

FIG. 9 is a view of a configuration of a measuring system according to a second embodiment. The measuring system illustrated in FIG. 9 includes the transmitting apparatus 1, the receiving apparatus 2, the detection apparatus 3 and a dosage apparatus 4. The transmitting apparatus 1, the receiving apparatus 2, the detection apparatus 3 according to the second embodiment are the same as those in the first embodiment. The dosage apparatus 4 is a medicine supply apparatus to consecutively (continuously) or intermittently supply a medicine in vivo. The dosage apparatus 4 may be used by being attached to regions instanced by an abdominal region, a brachial region and a gluteal region. The dosage apparatus 4 may take any one of a patch (paste) type and a tube type. The medicines include insulin and glucagon. The dosage apparatus 4 performs wireless data communications with the receiving apparatus 2, and also performs the wireless data communications with the detection apparatus 3. The dosage apparatus 4 may perform wired data communications with the receiving apparatus 2, and may also perform the wired data communications with the detection apparatus 3.

The transmitting apparatus 1 and the receiving apparatus 2, though configured as separate equipments in the second embodiment, may also be configured integrally. The transmitting apparatus 1 and the dosage apparatus 4, though configured as separate equipments in the second embodiment, may also be configured integrally. The receiving apparatus 2 and the dosage apparatus 4, though configured as separate equipments in the second embodiment, may also be configured integrally. The transmitting apparatus 1, the receiving apparatus 2 and the dosage apparatus 4 may also be configured integrally.

<Dosage Apparatus>

Figure 10:
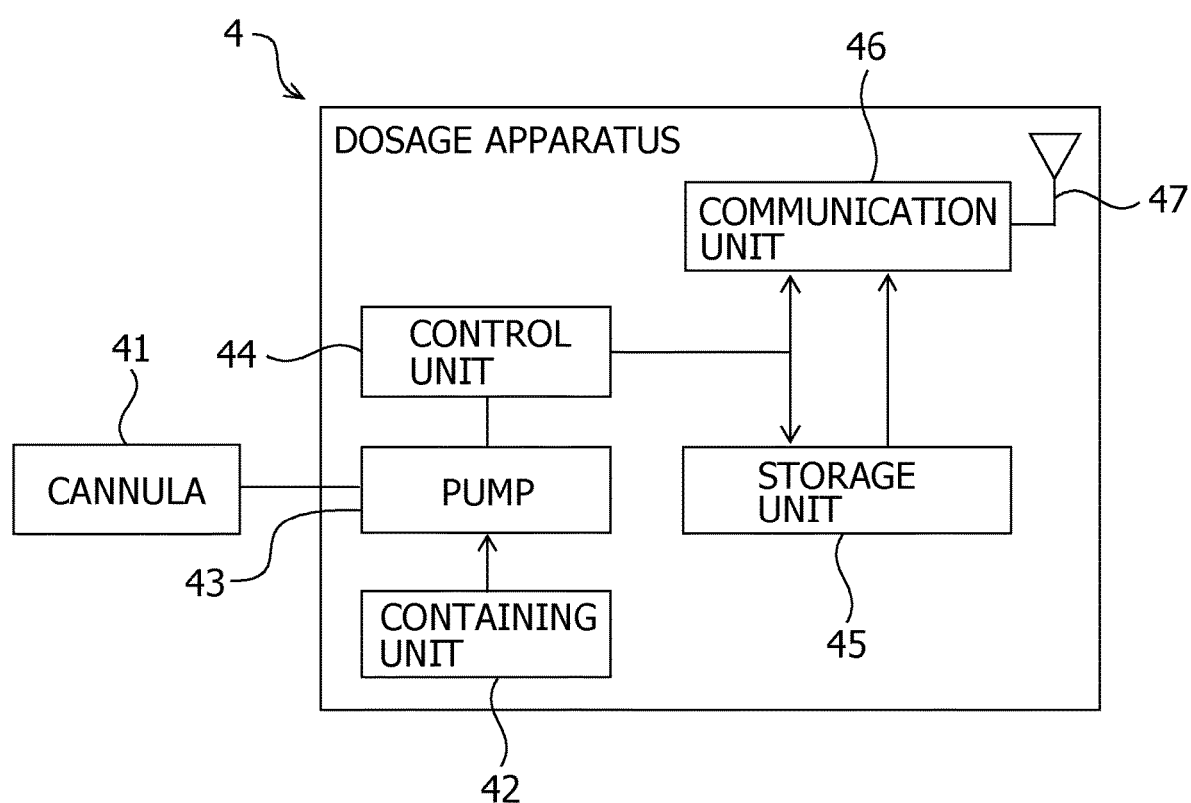
FIG. 10 is a block diagram of a configuration of a dosage apparatus according to the second embodiment.

The dosage apparatus 4 includes a cannula (insertion unit) 41 used by being implanted into a subcutaneous region of the user. The dosage apparatus 4 is pasted to a skin of the user by an adhesive tape and other equivalent materials, or is attached to a piece of clothing, a belt and other equivalent articles, thereby being attached to the user. FIG. 10 is a block diagram of a configuration of the dosage apparatus 4 according to the second embodiment. The dosage apparatus 4 includes, the cannula 41, a containing unit 42, a pump 43, a control unit (arithmetic unit) 44, a storage unit 45, a communication unit 46, and an antenna 47. The cannula 41 is connected to the pump 43. The containing unit 42 contains medicines. The containing unit 42 may contain plural types of medicines. A plurality of containing units 42 may also be provided in the dosage apparatus 4. For example, one of the plural containing units 42 may contain insulin, while another of the plural containing units 42 may also contain glucagon.

The pump 43 is actuated by, e.g., a motor and other equivalent devices. The pump 43 is actuated to feed the medicine within the containing unit 42 to the cannula 41, whereby the medicine is dosed in vivo. The pump 43 is one example of a "dosage unit". A plurality of pumps 43 may be provided in the dosage apparatus 4. For instance, one of the plural pumps 43 may be an insulin pump, while another of the plural pumps 43 may also be a glucagon pump. The control unit 44 controls the pump 43, the storage unit 45 and the communication unit 46. The control unit 44 receives various items of data from the receiving apparatus 2 and the detection apparatus 3 via the communication unit 46 and the antenna 47. The control unit 44 transmits the various items of data to the receiving apparatus 2 and detection apparatus 3 via the communication unit 46 and the antenna 47. The control unit 44, the storage unit 45 and the communication unit 46 may be attained by: computers each including the CPU, the RAM, the ROM and other equivalent hardware components that are provided in the dosage apparatus 4; respective apparatuses; and programs and other equivalent software components running on the computer.

The control unit 44 acquires the glucose concentration value in the interstitial fluid from the receiving apparatus 2. The control unit 44 may also acquire the response current value from the receiving apparatus 2. Calibration curve data representing a correspondence relation between the response current value and the glucose concentration value in the interstitial fluid, may be pre-stored in the storage unit 45. The control unit 44 may also acquire the glucose concentration value in the interstitial fluid by converting the response current value into the glucose concentration value with reference to the calibration curve data. The control unit 44 acquires the glucose concentration value in the blood from the receiving apparatus 2 or the detection apparatus 3. The control unit 44 may also acquire the current value from the receiving apparatus 2 or the detection apparatus 3. The calibration curve data representing a relation between the current value and the glucose concentration value in the blood may be pre-stored in the storage unit 45. The calibration curve data as, e.g., a mathematical expression and a correspondence table are pre-stored in the storage unit 45. The control unit 44 may also acquire the glucose concentration value in the blood by converting the current value into the glucose concentration value in the blood with reference to the calibration curve data.

The control unit 44 determines whether a pump 43 is actuated, based on the glucose concentration value in the interstitial fluid or the glucose concentration value in the blood. The following discussion will be focused on a case that the control unit 44 controls the pump 43 on the basis of the glucose concentration value in the interstitial fluid. The control unit 44 controls the pump 43 on the basis of the glucose concentration value in the blood, in which case the same control as the following control is carried out by replacing "the glucose concentration value in the blood" in the following discussion with "the glucose concentration value in the interstitial fluid".

The control unit 44 may determine whether the glucose concentration value in the interstitial fluid is equal to or larger than a predetermined value. The control unit 44 may also control the pump 43 so that the medicine is dosed in vivo when the glucose concentration value in the interstitial fluid is equal to or larger than the predetermined value. The control unit 44 may also determine whether the glucose concentration value in the interstitial fluid is less than the predetermined value. The control unit 44 may also control the pump 43 so that the medicine is dosed in vivo when the glucose concentration value in the interstitial fluid is less than the predetermined value. The control unit 44 may also determine whether the glucose concentration value in the interstitial fluid falls within a predetermined range. The control unit 44 may also control the pump 43 so that the medicine is dosed in vivo when the glucose concentration value in the interstitial fluid does not fall within the predetermined range.

The control unit 44 determines a type of medicine and a dosage (unit/min) of medicine, corresponding to the glucose concentration value in the interstitial fluid. The control unit 44 may determine whether the glucose concentration value in the interstitial fluid is equal to or larger than a first predetermined value. When the glucose concentration value in the interstitial fluid is equal to or larger than the first predetermined value, the control unit 44 may select the insulin as a dose medicine, and may control the pump 43 so that the insulin is dosed in vivo. The control unit 44 may determine whether the glucose concentration value in the interstitial fluid is equal to or less than a second predetermined value. When the glucose concentration value in the interstitial fluid is equal to or less than the second predetermined value, the control unit 44 may select glucagon as the dose medicine, and may control the pump 43 so that the glucagon is dosed in vivo.

The pump 43 is actuated to feed the medicine within the containing unit 42 to the cannula 41, thereby dosing the medicine in vivo. Upon dosing the medicine in vivo, the glucose concentration value in vivo increases or decreases due to an effect of the medicine. The glucose concentration value in the blood and the glucose concentration value in the interstitial fluid are thereby increased or decreased. Upon dosing the insulin in vivo, the glucose concentration value in the blood and the glucose concentration value in the interstitial fluid decreases. Upon dosing the glucagon in vivo, the glucose concentration value in the blood and the glucose concentration value in the interstitial fluid increases.

After dosing the medicine in vivo, the control unit 21 of the receiving apparatus 2 executes the first determination process or the second determination process. The first determination process and the second determination process are the same as those described in the first embodiment, and hence their repetitive explanations are omitted. Similarly to the first embodiment, the display unit 25 of the receiving apparatus 2 executes the process of displaying the recommendation information, the request information and the non-recommendation information, or executes the process of not displaying these items of information.

The control unit 44 may transmit a signal of starting the actuation of the pump 43 and a signal of finishing the actuation thereof to the receiving apparatus 2. The medicine is dosed in vivo, during which the display unit 25 may execute the process of not displaying the recommendation information and the request information. In other words, the medicine is dosed in vivo, during which the display unit 25 does not display the recommendation information and the request information. The medicine is dosed in vivo, during which the display unit 25 may execute the process of displaying the non-recommendation information.

Upon dosing the medicine in vivo, the glucose concentration value in vivo increases or decreases due to the effect of the medicine. In other words, when the medicine is dosed in vivo, the glucose concentration value in the blood and the glucose concentration value in the interstitial fluid increase or decrease. Due to the increase or decrease in glucose concentration value in the interstitial fluid, the variation in glucose concentration value in the interstitial fluid temporarily diminishes as the case may be. A fixed period of time is taken till the glucose concentration value in the interstitial fluid follows up the glucose concentration value in the blood. While the medicine is dosed in vivo, the user attached with the dosage apparatus 4 have an exercise, a meal and other equivalent actions to thereby increase or decrease the glucose concentration value in the blood, and the large variation in glucose concentration value in the blood is caused in some cases. Even when the in-blood glucose concentration value increases or decreases, the fixed period of time is taken till the glucose concentration value in the interstitial fluid increases or decreases. Accordingly, though the divergence exists between the glucose concentration value in the blood and the glucose concentration value in the interstitial fluid, the variation in glucose concentration value in the interstitial fluid is small as the case may be. In this case, it is unpreferable to calibrate the glucose reference value. While the medicine is dosed in vivo, the display unit 25 executes the process of not displaying the recommendation information and the request information. While the medicine is dosed in vivo, the display unit 25 executes the process of displaying the non-recommendation information. Implementation of calibrating the glucose reference value is thereby enabled to be avoided when there is the large variation in glucose concentration value in the blood.

The control unit 44 may determine whether the pump 43 is actuated, based on the glucose concentration value in the interstitial fluid and an increasing tendency or a decreasing tendency of the glucose concentration value in the interstitial fluid. The control unit 44 may also determine whether the glucose concentration value in the interstitial fluid within a first predetermined period has the increasing tendency. When the glucose concentration value in the interstitial fluid at an ending point of the first predetermined period increases over the glucose concentration value in the interstitial fluid at a starting point of the first predetermined period, the control unit 44 may determine that the glucose concentration value in the interstitial fluid within the first predetermined period has the increasing tendency. When the glucose concentration value in the interstitial fluid is equal to or larger than the first predetermined value and when the glucose concentration value in the interstitial fluid within the first predetermined period has the increasing tendency, the control unit 44 may control the pump 43 so that the insulin is dosed in vivo.

The control unit 44 may determine whether the glucose concentration value in the interstitial fluid within a second predetermined period has the decreasing tendency. When the glucose concentration value in the interstitial fluid at an ending point of the second predetermined period decreases under the glucose concentration value in the interstitial fluid at a starting point of the second predetermined period, the control unit 44 may determine that the glucose concentration value in the interstitial fluid within the second predetermined period has the decreasing tendency. When the glucose concentration value in the interstitial fluid is equal to or less than the second predetermined value and when the glucose concentration value in the interstitial fluid within the second predetermined period has the decreasing tendency, the control unit 44 may control the pump 43 so that the glucagon is dosed in vivo.

According to the second embodiment, the actuation of the pump 43 is controlled, and the medicine is dosed in vivo on the basis of the glucose concentration value in the interstitial fluid or the glucose concentration value in the blood. For example, when the glucose concentration in the interstitial fluid or the glucose concentration in the blood has the high value, the insulin is dosed in vivo, thereby decreasing the glucose concentration value in the interstitial fluid or the glucose concentration value in the blood. For instance, when the glucose concentration in the interstitial fluid or the glucose concentration in the blood has the low value, the glucagon is dosed in vivo, thereby increasing the glucose concentration value in the interstitial fluid or the glucose concentration value in the blood. Thus, it is feasible to keep, at a desired value, the glucose concentration value in the interstitial fluid or the glucose concentration value in the blood of the user.

FIG. 11 is a flowchart illustrating one example of a dose process in the dosage apparatus 4. For example, after switching ON the power source of the transmitting apparatus 1 and then switching ON the power source of the dosage apparatus 4, and transmitting apparatus 1 is initialized, and then the dosage apparatus 4 is initialized, thereby triggering a start of the flow illustrated in FIG. 11.

In step S11, the control unit 44 determines whether the pump 43 is actuated, based on the glucose concentration value in the interstitial fluid or the glucose concentration value in the blood. When actuating the pump 43, the processing proceeds to step S12. Whereas when not actuating the pump 43, the flow illustrated in FIG. 11 comes to an end. In step S12, the control unit 44 actuates the pump 43, whereby the medicine in the containing unit 42 is fed to the cannula 41 and is thus dosed in vivo.

The control unit 21 of the receiving apparatus 2 may also execute a part or a whole of the processes to be carried out by the control unit 44 of the dosage apparatus 4. For example, the control unit 21 may determine whether the pump 43 is actuated, based on the glucose concentration value in the interstitial fluid or the glucose concentration value in the blood. For instance, corresponding to the glucose concentration value in the interstitial fluid, the control unit 21 may determine the type and the dose quantity of the medicine, and may control the pump 43 so that the medicine is dosed in vivo.

For example, a program may be stored in a memory of the computer equipped in at least one of the transmitting apparatus 1, the receiving apparatus 2, detection apparatus 3 and the dosage apparatus 4, and may be run by the computer, whereby there respective processes in the first through third embodiments may also be attained. The computer may include a processor instanced by the CPU, a Micro Processing Unit (MPU) and a Field Programmable Gate Array (FPGA), and may also include a dedicated processor instanced by an Application Specific Integrated Circuit (ASIC). The respective processes in the first through third embodiments may be attained based on a method by which the computer runs the program. The program may be provided to the computer via, e.g., a network or from a computer readable recording medium and other equivalent mediums that retain the data in a non-transitory manner. The program may be recorded on the computer readable recording medium.

<Computer Readable Recording Medium>

It is possible to record a program which causes a computer, machine, system (hereinafter, described as computer and other equivalent hardware components) to implement any of the functions described above on a computer readable recording medium. By causing the computer and other equivalent hardware components to read in the program from the recording medium and execute it, the function thereof can be provided. The computer readable recording medium mentioned herein indicates a recording medium which stores information such as data and a program by an electric, magnetic, optical, mechanical, or chemical operation and allows the stored information to be read from the computer and other equivalent hardware components. Of such recording media, those detachable from the computer or the like include, e.g., a flexible disk, a magneto-optical disk, a CD-ROM, a CD-R/W, a DVD, a Blu-ray disc, a DAT, an 8-mm tape, a flash memory and a memory card. Of such recording media, those fixed to the computer and other equivalent hardware components include a hard disk, a ROM or the like.

What is claimed is:

1. A measuring apparatus comprising:
a measuring unit including electrodes configured to measure signal values corresponding to a concentration of a specified substance contained in a first sample in vivo of a user;
an acquiring unit configured to acquire a reference concentration value pertaining to the specified substance contained in a second sample in vitro;
a calculation unit configured to calculate initial concentration values of the specified substance contained in the first sample based on the signal values;
a determination unit configured to determine whether a variation in the initial concentration values of the specified substance contained in the first sample is equal to or less than a threshold value;
a display unit; and
an output unit configured to keep outputting, to the display unit, recommendation information which is information for recommending the user for acquiring the reference concentration value while the variation in the initial concentration values of the specified substance contained in the first sample is equal to or less than the threshold value,
wherein, responsive to the recommendation information, the reference concentration value is acquired using the acquiring unit, and one of the initial concentration values is corrected using the calculation unit based on the reference concentration value to obtain a corrected concentration value of the specified substance contained in the first sample.

2. The measuring apparatus according to claim 1, wherein the concentration value of the specified substance contained in the first sample is not displayed on the display unit.

3. The measuring apparatus according to claim 1, wherein the output unit does not output the recommendation information to the display unit in response to a determination that the variation in the concentration value of the specified substance contained in the first sample is larger than the threshold value.

4. The measuring apparatus according to claim 1, wherein the output unit outputs, to the display unit, non-recommendation information representing non-recommendation for acquiring the reference concentration value in response to a determination that the variation in the concentration value of the specified substance contained in the first sample is larger than the threshold value.

5. The measuring apparatus according to claim 1, further comprising:
a control unit configured to control a dose unit configured to dose a medicine in vivo, wherein the control unit controls the dose unit to dose the medicine in vivo, based on the reference concentration value or the concentration value of the specified substance contained in the first sample.

6. The measuring apparatus according to claim 5, wherein the medicine includes insulin, the control unit determines whether the reference concentration value or the concentration value of the specified substance contained in the first sample is equal to or larger than a first predetermined value, the control unit determines whether the reference concentration value or the concentration value of the specified substance contained in the first sample has an increasing tendency within a first predetermined period, and the control unit controls the dose unit to dose the insulin in vivo in response to a determination that the reference concentration value or the concentration value of the specified substance contained in the first sample is equal to or larger than the first predetermined value and in response to a determination that the reference concentration value or the concentration value of the specified substance contained in the first sample has the increasing tendency within the first predetermined period.

7. The measuring apparatus according to claim 5, wherein the medicine includes glucagon, the control unit determines whether the reference concentration value or the concentration value of the specified substance contained in the first sample is equal to or less than a second predetermined value, the control unit determines whether the reference concentration value or the concentration value of the specified substance contained in the first sample has a decreasing tendency within a second predetermined period, and the control unit controls the dose unit to dose the glucagon in vivo in response to a determination that the reference concentration value or the concentration value of the specified substance contained in the first sample is equal to or less than the second predetermined value and in response to a determination that the reference concentration value or the concentration value of the specified substance contained in the first sample has the decreasing tendency within the second predetermined period.

8. The measuring apparatus according to claim 1, wherein
  the determination unit is configured to further determine whether a variation in the concentration value of the specified substance contained in the first sample is larger than the threshold value; and
  the output unit is configured to further output, to a display unit, non-recommendation information representing non-recommendation for acquiring the reference concentration value in response to a determination that the variation in the concentration value of the specified substance contained in the first sample is larger than the threshold value.

9. The measuring apparatus according to claim 8, wherein the concentration value of the specified substance contained in the first sample is not displayed on the display unit.

10. The measuring apparatus according to claim 8, wherein the output unit does not output the non-recommendation information to the display unit in response to a determination that the variation in the concentration value of the specified substance contained in the first sample is equal to or less than the threshold value.

11. A non-transitory computer-readable medium storing a measuring program for causing a computer to execute:
  a process of measuring signal values corresponding to a concentration of a specified substance contained in a first sample in vivo of a user;
  a process of calculating initial concentration values of the specified substance contained in the first sample based on the signal values;
  a process of determining whether a variation in the initial concentration values of the specified substance contained in the first sample is equal to or less than a threshold value;
  a process of keep outputting, to a display unit, recommendation information which is information for recommending the user to acquire a reference concentration value pertaining to the specified substance contained in a second sample in vitro while the variation in the initial concentration values of the specified substance contained in the first sample is equal to or less than the threshold value; and
  responsive to the recommendation information, a process of acquiring the reference concentration value, and a process of correcting one of the initial concentration values based on the reference concentration value to obtain a corrected concentration value of the specified substance contained in the first sample.

12. The non-transitory computer-readable medium storing the measuring program according to claim 11, wherein the concentration value of the specified substance contained in the first sample is not displayed on the display unit.

13. The non-transitory computer-readable medium storing a measuring program according to claim 11, wherein the program causes the computer to further execute:
  a process of determining whether a variation in the concentration value of the specified substance contained in the first sample is larger than the threshold value; and
  a process of outputting, to a display unit, non-recommendation information representing non-recommendation for acquiring the reference concentration value in response to a determination that the variation in the concentration value of the specified substance contained in the first sample is larger than the threshold value.

14. The non-transitory computer-readable medium storing the measuring program according to claim 13, wherein the concentration value of the specified substance contained in the first sample is not displayed on the display unit.

15. A measuring method comprising:
  a process of measuring signal values corresponding to a concentration of a specified substance contained in a first sample in vivo of a user;
  a process of calculating initial concentration values of the specified substance contained in the first sample based on the signal values;
  a process of determining whether a variation in the initial concentration values of the specified substance contained in the first sample is equal to or less than a threshold value;
  a process of keep outputting, to a display unit, recommendation information which is information for recommending the user to acquire a reference concentration value pertaining to the specified substance contained in a second sample in vitro while the variation in the initial concentration values of the specified substance contained in the first sample is equal to or less than the threshold value; and
  responsive to the recommendation information, a process of acquiring the reference concentration value, and a process of correcting one of the initial concentration values based on the reference concentration value to obtain a corrected concentration value of the specified substance contained in the first sample.

16. The measuring method according to claim 15, wherein the concentration value of the specified substance contained in the first sample is not displayed on the display unit.

17. The measuring method according to claim 15 further comprising:
  a process of determining whether a variation in the concentration value of the specified substance contained in the first sample is larger than the threshold value; and
  a process of outputting, to a display unit, non-recommendation information representing non-recommendation for acquiring the reference concentration value in response to a determination that the variation in the concentration value of the specified substance contained in the first sample is larger than the threshold value.

18. The measuring method according to claim 17, wherein the concentration value of the specified substance contained in the first sample is not displayed on the display unit.

\* \* \* \* \*